(12) United States Patent
Pautsch et al.

(10) Patent No.: US 10,799,196 B2
(45) Date of Patent: Oct. 13, 2020

(54) SYSTEM AND METHOD FOR ENCOURAGING PATIENT STILLNESS DURING IMAGING

(71) Applicant: General Electric Company, Schenectady, NY (US)

(72) Inventors: Adam Gregory Pautsch, Oconomowoc, WI (US); Erik Paul Kemper, Franklin, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 437 days.

(21) Appl. No.: 15/818,106

(22) Filed: Nov. 20, 2017

(65) Prior Publication Data
US 2019/0150862 A1   May 23, 2019

(51) Int. Cl.
*G09B 5/06* (2006.01)
*A61B 6/04* (2006.01)
*A61B 5/11* (2006.01)
*A61B 5/00* (2006.01)
*A61B 5/103* (2006.01)
*H04R 1/02* (2006.01)

(52) U.S. Cl.
CPC .......... *A61B 6/0492* (2013.01); *A61B 5/1114* (2013.01); *A61B 5/486* (2013.01); *A61B 5/742* (2013.01); *G09B 5/06* (2013.01); *A61B 5/1036* (2013.01); *A61B 5/11* (2013.01); *A61B 5/6802* (2013.01); *A61B 5/6891* (2013.01); *A61B 2562/0219* (2013.01); *A61B 2562/0247* (2013.01); *H04R 1/028* (2013.01); *H04R 2499/15* (2013.01)

(58) Field of Classification Search
CPC .............. G01R 33/56509; G01R 33/567–5676
See application file for complete search history.

(56) References Cited

U.S. PATENT DOCUMENTS

| | | | |
|---|---|---|---|
| 5,645,077 A | 7/1997 | Foxlin | |
| 5,830,143 A * | 11/1998 | Mistretta et al. | A61B 5/055 600/422 |
| 5,966,680 A | 10/1999 | Butnaru | |
| 6,734,834 B1 | 5/2004 | Baram | |
| 6,736,511 B2 | 8/2004 | Plummer et al. | |

(Continued)

OTHER PUBLICATIONS https://www.youtube.com/watch?v=Oh66nKHMgp8. Don't Stumble Tumble—MRI Preparation Application, Published on Nov. 27, 2014.

*Primary Examiner* — Robert J Utama
(74) *Attorney, Agent, or Firm* — Fletcher Yoder, P.C.

(57) ABSTRACT

A system for encouraging patient stillness during an imaging scan is provided. The system includes an electronic device configured to generate a graphical representation for a patient undergoing the imaging scan. The system also includes a motion detection system configured to detect motion of the patient undergoing the imaging scan. The system further includes a computer system in communication with the electronic device and the motion detection system, wherein the computer system includes processing circuitry configured to receive a first signal from the motion detection system indicating motion of the patient undergoing the imaging scan and to send a second signal to the electronic device, in response to the first signal, to cause the electronic device to adversely modify the display of the graphical representation.

7 Claims, 3 Drawing Sheets

(56) References Cited

U.S. PATENT DOCUMENTS

| | | |
|---|---|---|
| 8,692,845 B2 | 4/2014 | Fedorovskaya et al. |
| 9,646,574 B2 | 5/2017 | Hoellwarth |
| 2005/0107685 A1* | 5/2005 | Seeber .................. A61B 5/055 600/422 |
| 2012/0108909 A1 | 5/2012 | Slobounov et al. |
| 2013/0245424 A1* | 9/2013 | deCharms .......... G01R 33/4806 600/410 |
| 2014/0229410 A1 | 8/2014 | Jallon et al. |

* cited by examiner

SYSTEM AND METHOD FOR ENCOURAGING PATIENT STILLNESS DURING IMAGING

BACKGROUND

The subject matter disclosed herein relates to medical imaging and, in particular, to a system and method for encouraging patient stillness during imaging.

Sometimes conducting imaging scans may be difficult, especially for pediatric patients. For example, young patients may not understand the scan and it could be difficult to keep them still. Also, the patient may be nervous. Unwanted movement may cause artifacts in the imaging data. This may result in needing to perform additional scans (increasing the exposure to radiation), while also increasing the amount of time and effort in acquiring quality image data. In addition, it results in having to block off more time for use of the scanner (e.g., for pediatric scans).

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In accordance with a first embodiment, a system for encouraging patient stillness during an imaging scan is provided. The system includes an electronic device configured to generate a graphical representation for a patient undergoing the imaging scan. The system also includes a motion detection system configured to detect motion of the patient undergoing the imaging scan. The system further includes a computer system in communication with the electronic device and the motion detection system, wherein the computer system includes processing circuitry configured to receive a first signal from the motion detection system indicating motion of the patient undergoing the imaging scan and to send a second signal to the electronic device, in response to the first signal, to cause the electronic device to adversely modify the display of the graphical representation.

In accordance with a second embodiment, a method for encouraging patient stillness during an imaging scan is provided. The method includes generating, via an electronic device, a graphical representation for a patient undergoing the imaging scan. The method also includes monitoring, via a motion detection system, motion of the patient undergoing the imaging scan. The method further includes receiving, at processing circuitry, a first signal from the motion detection system indicating motion of the patient undergoing the imaging scan. The method even further includes sending, via the processing circuitry, a second signal to the electronic device, in response to the first signal, to cause the electronic device to adversely modify the display of the graphical representation.

In accordance with a third embodiment, a system for encouraging patient stillness during an imaging scan is provided. The system includes a headset including a display, wherein the headset is configured to be worn by a patient and to generate a graphical representation on the display for the patient when undergoing the imaging scan. The system also includes a motion detection system configured to detect motion of the patient undergoing the imaging scan. The system further includes a computer system in communication with the headset and the motion detection system, wherein the computer system includes processing circuitry configured to receive a first signal from the motion detection system indicating motion of the patient undergoing the imaging scan and to send a second signal to the headset, in response to the first signal, to cause the headset to adversely modify the display of the graphical representation.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
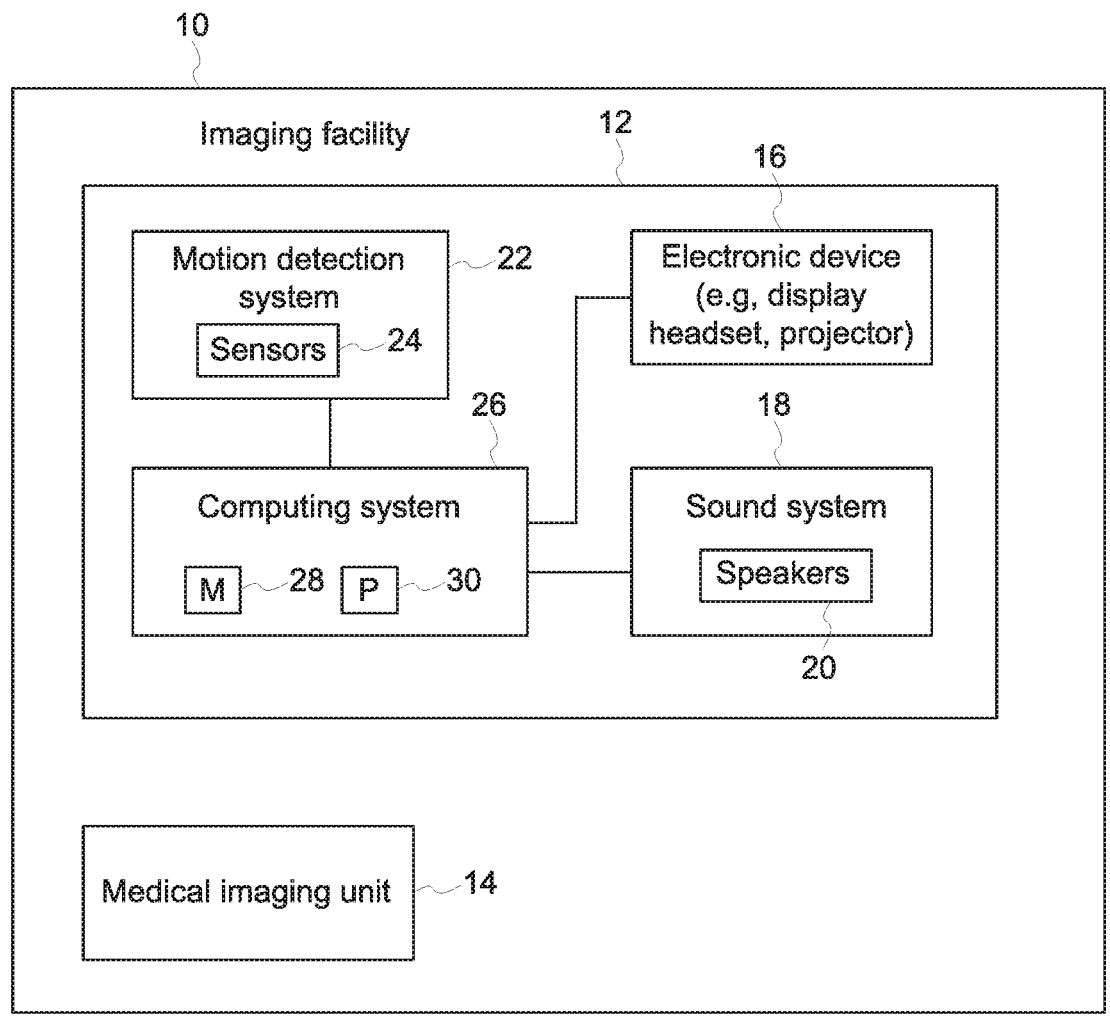
FIG. 1 is a schematic diagram of an embodiment of an imaging facility including a system for encouraging patient stillness during an imaging scan.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Disclosed herein are systems and methods for encouraging patient stillness during an imaging scan. In certain embodiments, a graphical representation (e.g., images or movies) and/or sound are provided for the distraction of the patient when attempting to acquire image data during an imaging scan. A motion detection system may monitor the patient for any undesired motion or movement (voluntary and/or involuntary). If any undesired patient motion deemed sufficient enough to affect the image quality is acquired, the graphical representation may be adversely modified (e.g., ceased, grow/shrink, degressed, defeatured, etc.) for a given amount of time or until the undesired patient motion has ceased. If sound is also provided, it may be adversely modified (e.g. faded or made quiet). Upon the passing of time or the undesired patient motion, the graphical representation and/or sound may be resumed and the imaging data acquired while the patient is sufficiently still. In certain embodiments, the graphical representation may be provided to the patient via a headset (e.g., virtual reality headset) worn by the patient that provides the graphical representation and/or sound. In certain embodiments, the graphical representation may be provided by a projection system. The disclosed embodiments may improve workflow by reducing the number of scans and/or time to proceed with the scan as well as reduce the time set aside for utilizing the medical imaging system (e.g., computed tomography (CT) system, magnetic resonance (MR) imaging system, X-ray system, ultrasound system, positron emission tomography (PET) system, etc.). In addition, the amount of radiation the patient is exposed to may be reduced (e.g., due to fewer scans).

FIG. 1 is a schematic diagram of an embodiment of an imaging facility 10 (e.g., imaging room) including a system 12 for encouraging patient stillness during an imaging scan. In addition, the imaging facility 10 includes a medical imaging unit 14 for performing the imaging scan to acquire image data of a patient. The medical imaging unit 14 may be for a CT system, MR imaging system, an X-ray system, an ultrasound system, a PET system, or any other type of medical imaging system. The system 12 includes an electronic device 16 for providing a graphical representation (e.g., images, video images, movie, etc.) to a patient during an imaging scan. The system 12 also includes a sound system 18 having at least one speaker 20 for providing audio to accompany the graphical representation during the imaging scan.

In certain embodiments, the electronic device 16 may include a display headset (e.g., virtual reality, augmented reality, or 90 degree mirror glasses) configured to be worn on the head of the patient. The display headset may include a display for providing the graphical representation to the patient. The display headset may also include the sound system 18 for providing the audio accompanying the graphical representation. In certain embodiments, the display headset may also include a tracking system (e.g., tracking sensors) to monitor patient motion, or regions to be selected based on the scan to be performed (e.g., head and shoulders for head but allowing hand and feet motion).

In certain imaging operations (e.g., CT head scans or MR scans), wearing a headset may interfere with the imaging system. Thus, alternatively, the electronic device 16 may include a projector configured to generate and project the graphical representation on a location within the imaging facility or room 10 visible to the patient. For example, the projector may be configured to project the graphical representation on a wall or screen within the imaging room and/or a surface of a bore of the medical imaging unit 14. In this case, the one or more speakers 20 of the sound system 18 may disposed throughout the room 10 and/or on the medical imaging unit 14 to provide the audio accompanying the graphical representation.

The system 12 also includes a motion detection system 22 configured to detect the motion of a patient undergoing the imaging scan. The motion detection system 22 may include one or more sensors 24 (e.g., tracking tags, accelerometers, pressure sensors, etc.) disposed on the patient and/or over the patient (e.g., on or within sheets, blankets, garments, etc.). In certain embodiments, pressure sensors may be disposed within a table that the patient is positioned on to detect patient motion. In certain embodiments, sheets, blankets, and/or garments disposed on or over a patient may include conductive fabric to detect patient motion. In certain embodiments, laser sweep technology (infrared LEDs, etc.) may be utilized to detect patient motion. In certain embodiments, an accelerometer tracking system may be utilized to detect patient motion. In certain embodiments, a camera or depth of field based motion detection system may be utilized to detect patient motion. In certain embodiments, a tracking system within the virtual reality headset may be utilized to detect patient motion (e.g., of the head).

The electronic device 16, the sound system 18, and the motion detection system 22 may be in communication (e.g., electronic communication) with a computer system 26 (e.g., computing device such a tablet, smart phone, computer, etc.). In certain embodiments, the communication may be wired. In other embodiments, the communication may be wirelessly (e.g., via transmitters). In certain embodiments, the computer system 26 may be part of an imaging system that includes the medical imaging unit 14 and may be utilized to provide commands to the medical imaging unit 14. The computer system 26 includes a memory 28 and a processor 30 to execute code or instructions stored within the memory 28. The instructions stored on the memory 28 may be encoded in programs or codes stored in a tangible non-transitory computer-readable medium. The memory 28 may include a computer readable medium, such as, without limitation, a hard disk drive, a solid state drive, diskette, flash drive, a compact disc, a digital video disc, random access memory (RAM), and/or any suitable storage device that enables the processor 30 to store, retrieve, and/or execute instructions and/or data. The processor 30 may be a general purpose processor (e.g., processor of a desktop/laptop computer), system-on-chip (SoC) device, or application-specific integrated circuit, or some other processor configuration.

The processor 30 is configured to monitor the patient motion upon the patient being readied for the imaging scan. For example, the processor 30 is configured to receive one or more signals from the motion detection system 22 (e.g., from the sensors 24) indicating motion of the patient undergoing the imaging scan. In certain embodiments, the processor 30, in conjunction with the motion detection system 22, is configured to determine a magnitude of the patient motion. In certain embodiments, the processor 30, in conjunction with the motion detection system 22, is configured to determine if the patient motion is voluntary or involuntary. In certain embodiments, the processor 30 is configured to determine whether detected patient motion is significant enough to affect image quality (e.g., by comparing the detected patient motion to a specified threshold or range). If the patient motion is significant enough, the processor 30 is configured to send a signal to the electronic device 16 to blur or cease (e.g., fade to black or defeatured) providing the graphical representation to the patient for a given period of time or until the patient has stopped moving or the patient motion is not significant enough to affect image quality. In certain embodiments, the given period of time for blurring or ceasing the graphical representation may be based on a magnitude and/or frequency of the patient motion. For example, a large movement or frequent movement by the patient may increase the period of time. The processor 30 is configured to provide a subsequent signal to the electronic device 18 to deblur or resume the graphical representation provided to the patient after the period of time has passed or the patient has stopped moving or the patient motion is not significant enough to affect image quality. If the patient motion is not significant enough, the processor 30 will not send a signal to the electronic device 16 to blur or cease providing the graphical representation. Instead, the quality of the graphical representation provided to the patient will be maintained or will increase. In certain embodiments, the processor 30 may similarly regulate the sound system 18 in providing the accompanying audio to the graphical representation to the patient based on patient motion.

Figure 2:
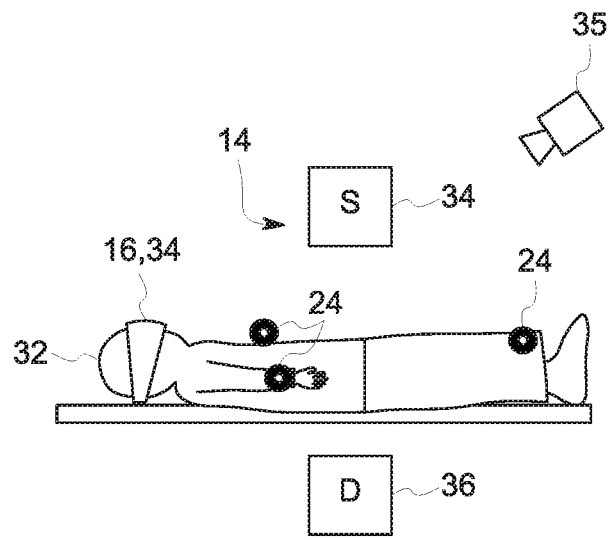
FIG. 2 is a schematic diagram of an embodiment of a patient wearing a display headset during an imaging scan.

FIG. 2 is a schematic diagram of an embodiment of a patient wearing a virtual reality headset during an imaging scan. As depicted, a patient 32 is positioned between an X-ray source 34 and a detector 36 of the medical imaging unit 14. As depicted, the patient 32 is wearing a display headset 34 (e.g., virtual reality, augmented reality, or 90 degree mirror glasses). The display headset 34 may include a display for providing the graphical representation to the patient 32. The display headset may also include the sound system 18 for providing the audio accompanying the graphical representation. In certain embodiments, the display headset 34 may also include a tracking system (e.g., tracking sensors) to monitor patient head motion. As depicted, sensors 24 are disposed on the patient (e.g., wearable bracelets, fabric-integrated sensors, etc.) to aid in detecting motion. In certain embodiments, as depicted, a camera or depth of field sensor 35 may be utilized to monitor patient motion. The display headset 34 in conjunction with the motion detection system 22 and the computing system 26 discourages patient motion as described above.

Figure 3:
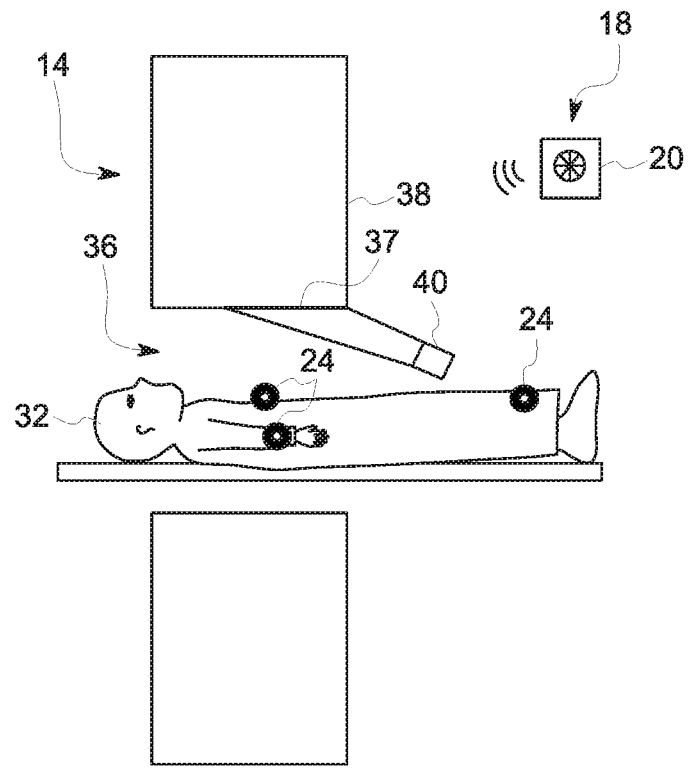
FIG. 3 is a schematic diagram of an embodiment of a projection system utilized to provide a graphical representation to a patient during an imaging scan.

FIG. 3 is a schematic diagram of an embodiment of a projection system utilized to provide a graphical representation to a patient during an imaging scan. As depicted, the patient 32 is positioned within a bore 36 of a gantry 38 of the medical imaging unit 14 (e.g., CT imaging unit). As depicted, the graphical presentation 37 is projected onto a surface of the bore 36 via a projector 40. In certain embodiments, the graphical representation may be projected, via the projector 40, on a wall or screen within the imaging room that is visible to the patient 32. As depicted, audio is provided to accompany the graphical representation via the speaker 20 of the sound system 18. One or more speakers may be disposed throughout the imaging room or disposed on the imaging unit 14. The projector 40 and sound system 18 in conjunction with the motion detection system 22 and the computing system 26 discourages patient motion as described above.

Figure 4:
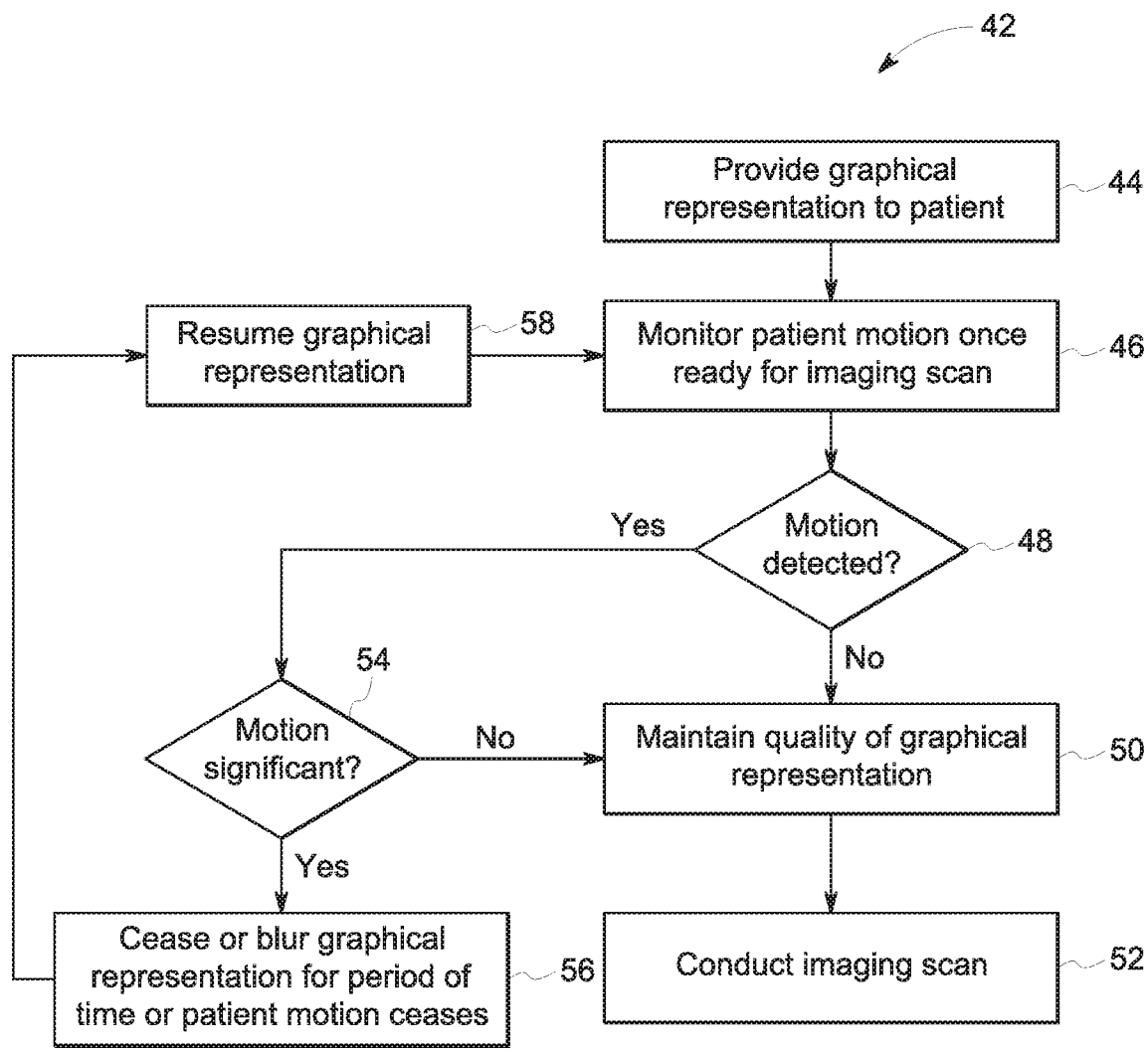
FIG. 4 is a flow chart of an embodiment of a method for encouraging patient stillness during an imaging scan.

FIG. 4 is a flow chart of an embodiment of a method 42 for encouraging patient stillness during an imaging scan. The steps of the method 42 may be performed by the components of the system 12 and/or medical imaging unit 14 described above. Some of the steps of the method 42 may be performed simultaneously or in a different order from that depicted in FIG. 4. The method 42 includes providing a graphical representation to the patient 32 (block 44). The graphical representation is provided via the electronic device 16 (e.g., display headset or projector). This may occur in a different room (e.g., for the display headset) before the patient is transferred to the imaging room. In certain embodiments, audio is provided to accompany the graphical representation via the sound system 18. For example, the electronic device 16 may include speakers 20 (e.g., incorporated within the virtual reality headset) or the speakers 20 may distributed within the imaging room 10 (e.g., when the projector is utilized). In certain embodiments, when the patient is in a different room prior to being transferred to the imaging room, audio may be provided that incorporates sounds of the scanner to get the patient use to the sound to reduce anxiety.

The method 42 also includes monitoring patient motion prior to and during the imaging scan session (block 46). Monitoring the motion prior to the imaging scan session enables the patient to get use to trying to stay still. Once the patient 32 is set within the preferred position for the scan, the patient motion is monitored in earnest to perform the scan. The patient motion is monitored with the motion detection system 22 described above. The method 42 includes determining if motion is detected (block 48). For example, the processor 30 of the computing system 26 may receive one or more signals from the motion detection system 22 (e.g., sensors 24) representative of potential patient motion. If no patient motion is detected, the method 42 includes maintaining the quality of the graphical representation provided to the patient 32 (as well as continuing to provide accompanying audio) (block 50). While the patient 32 is still (at least still enough to not affect image quality), the method 42 includes conducting the imaging scan to acquire image data (block 52).

If patient motion is detected, the method 42 includes determining if the motion is significant (e.g., would affect image quality) (block 54). In certain embodiments, the detected patient motion (e.g., the signals or a variable derived from the signals) may be compared to a specified threshold or range or allow motion in regions that will not affect image quality. If the motion is not significant (e.g., would not affect image quality), the method 42 includes maintaining the quality of the graphical representation (block 50) and conducting the imaging scan (block 52). If the motion is significant (e.g., would affect image quality), the method 42 includes adversely modifying (e.g., ceasing, fading to black, defeaturing or blurring) the graphical representation (via a signal sent to the electronic device 16) for a period of time or until patient motion has ceased or is not significant enough to affect image quality (block 56). With regard to defeaturing, a patient may be able to choose some elements that will at different stages be added in the graphical representation to encourage the patient to stay sill longer. However, if the patient moves some of these features may go away. For example, a graphical representation may initially include a tree that starts out bare, grows leaves and/or flowers over time, and a bird may visit and build a nest. If motion is detected, the leaves will fall and the tree may become bare again. Another example, may include a pond that starts empty but fish, frogs, and other wildlife may be added if the patient remains still. If the patient moves, these features may be removed. In certain embodiments, the audio accompanying the graphical representation may also be ceased. In certain embodiments, the given period of time for adversely modifying the graphical representation may be based on a magnitude and/or frequency of the patient motion. For example, a large movement or frequent movement by the patient may increase the period of time. Once the period of time has passed or patent motion has ceased or is not significant enough to affect image quality, the method 42 includes resuming providing the graphical representation and audio to the patient 32 (via signals sent to the electronic device 16 and/or sound system 18) (block 58), while monitoring patient motion (block 46).

Technical effects of the disclosed embodiments include encouraging patient stillness during an imaging scan by providing a graphical representation (e.g., images or movies) and/or sound for the distraction of the patient when attempting to acquire image data during an imaging scan. If any undesired patient motion deemed sufficient enough to affect the image quality is acquired, the graphical representation may be adversely modified (e.g., blurred, faded to black, or ceased) for a given amount of time or until the undesired patient motion has ceased. The graphical representation and/or sound may be resumed and the imaging data acquired when the patient is sufficiently still. The disclosed embodiments may improve workflow by reducing the number of scans and/or time to proceed with the scan as well as reduce the time set aside for utilizing the medical imaging system (e.g., computed tomography system, magnetic resonance imaging system, X-ray system, etc.). In addition, the amount of radiation the patient is exposed may be reduced (e.g., due to fewer scans).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system for encouraging patient stillness during an imaging scan, comprising:
    an electronic device configured to generate a graphical representation for a patient undergoing the imaging scan;
    a motion detection system configured to detect motion of the patient undergoing the imaging scan;
    a computer system in communication with the electronic device and the motion detection system, wherein the computer system comprises processing circuitry configured to receive a first signal from the motion detection system indicating motion of the patient undergoing the imaging scan and to send a second signal to the electronic device, in response to the first signal, to cause the electronic device to adversely modify the display of the graphical representation; and
    a speaker of a sound system configured to generate audio to accompany the graphical representation during the imaging scan, wherein the processing circuitry is configured to send a third signal to the sound system to cause the sound system to cease providing audio in response to detection of patient motion.

2. The system of claim 1, wherein the electronic device comprises a display headset configured to be worn by the patient, wherein the display headset comprises a display for showing the graphical representation.

3. The system of claim 1, wherein the electronic device comprises a projector configured to generate the image within a location where the imaging scan is occurring.

4. A method for encouraging patient stillness during an imaging scan, comprising:
    generating, via an electronic device, a graphical representation for a patient undergoing the imaging scan;
    monitoring, via a motion detection system, motion of the patient undergoing the imaging scan;
    receiving, at processing circuitry, a first signal from the motion detection system indicating motion of the patient undergoing the imaging scan;
    sending, via the processing circuitry, a second signal to the electronic device, in response to the first signal, to cause the electronic device to adversely modify the display of the graphical representation; and
    sending, via the processing circuitry, a third signal to a sound system comprising a speaker that causes the sound system to cease providing audio accompanying the graphical representation in response to detection of patient motion.

5. The method of claim 4, wherein the electronic device comprises a display headset configured to be worn by the patient, wherein the display headset comprises a display for showing the graphical representation.

6. The method of claim 4, wherein the electronic device comprises a projector configured to generate the image within a location where the imaging scan is occurring.

7. A system for encouraging patient stillness during an imaging scan, comprising:
    a display headset comprising a display, wherein the display headset is configured to be worn by a patient and to generate a graphical representation on the display for the patient when undergoing the imaging scan;
    a motion detection system configured to detect motion of the patient undergoing the imaging scan; and
    a computer system in communication with the display headset and the motion detection system, wherein the computer system comprises processing circuitry configured to receive a first signal from the motion detection system indicating motion of the patient undergoing the imaging scan and to send a second signal to the display headset, in response to the first signal, to cause the display headset to adversely modify the display of the graphical representation;
    wherein the virtual reality headset comprises a speaker configured to generate audio that accompanies the graphical representation when the patient is undergoing the imaging scan, and the processing circuitry is configured to send a third signal to the speaker that causes the speaker to cease providing audio accompanying the graphical representation in response to detection of patient motion.

* * * * *